(12) United States Patent
Yu

(10) Patent No.: US 12,324,644 B2
(45) Date of Patent: *Jun. 10, 2025

(54) REGULATING JOINT SPACE VELOCITY OF A SURGICAL ROBOTIC ARM

(71) Applicant: Verb Surgical Inc., Santa Clara, CA (US)

(72) Inventor: Haoran Yu, Sunnyvale, CA (US)

(73) Assignee: Verb Surgical Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/440,829

(22) Filed: Feb. 13, 2024

(65) Prior Publication Data

US 2024/0245477 A1    Jul. 25, 2024

Related U.S. Application Data

(63) Continuation of application No. 17/575,383, filed on Jan. 13, 2022, now Pat. No. 11,918,312, which is a
(Continued)

(51) Int. Cl.
*A61B 34/30*        (2016.01)
*A61B 34/00*        (2016.01)
(Continued)

(52) U.S. Cl.
CPC ............. *A61B 34/37* (2016.02); *A61B 34/25* (2016.02); *A61B 34/70* (2016.02); *A61B 1/3132* (2013.01)

(58) Field of Classification Search
USPC .................................................. 700/245–264
See application file for complete search history.

(56) References Cited

U.S. PATENT DOCUMENTS 6,092,004 A * 7/2000 Harima .............. G05B 19/4103
                                                        700/250
6,317,651 B1 * 11/2001 Gerstenberger ....... B25J 9/1664
                                                        700/245
(Continued)

FOREIGN PATENT DOCUMENTS

KR    10-2015-0126951 A    11/2015
KR    10-2015-0133756 A    11/2015
(Continued)

OTHER PUBLICATIONS

Office Action received for Japanese Patent Application No. 2022-523939, mailed on Jul. 2, 2024, 12 pages (6 pages of English Translation and 6 pages of Original Document).
(Continued)

*Primary Examiner* — Jonathan L Sample
(74) *Attorney, Agent, or Firm* — Aikin & Gallant, LLP

(57) ABSTRACT

A surgical robotic system has a surgical robotic arm, and a programmed processor that determines a longest principal axis of a velocity ellipsoid for a first configuration of the arm, applies a maximum task space velocity (that is in the direction of the longest principal axis) to an inverse kinematics equation which computes a potential joint space velocity, computes a ratio of i) the potential joint space velocity and ii) a joint space velocity limit of the arm, and applies the ratio to an initial joint space velocity, to produce a regulated joint space velocity. Other aspects are also described and claimed.

20 Claims, 4 Drawing Sheets

Related U.S. Application Data continuation of application No. 16/663,277, filed on Oct. 24, 2019, now Pat. No. 11,229,494.

(51) Int. Cl.
*A61B 34/37* (2016.01)
*A61B 1/313* (2006.01)

(56) References Cited

U.S. PATENT DOCUMENTS

| | | | | |
|---|---|---|---|---|
| 6,493,608 | B1* | 12/2002 | Niemeyer | A61B 34/70 700/255 |
| 7,257,237 | B1* | 8/2007 | Luck | G06T 7/251 382/103 |
| 7,741,802 | B2* | 6/2010 | Prisco | B25J 9/1689 318/632 |
| 8,060,250 | B2* | 11/2011 | Reiland | B25J 9/1633 901/29 |
| 9,468,501 | B2* | 10/2016 | Hourtash | A61B 18/14 |
| 10,314,661 | B2* | 6/2019 | Bowling | A61B 34/32 |
| 11,229,494 | B2* | 1/2022 | Yu | A61B 34/37 |
| 11,285,603 | B2* | 3/2022 | Yamada | B25J 9/1669 |
| 11,918,312 | B2* | 3/2024 | Yu | G16H 20/40 |
| 2003/0029463 | A1 | 2/2003 | Niemeyer | |
| 2006/0258938 | A1* | 11/2006 | Hoffman | A61B 5/06 600/424 |
| 2007/0151389 | A1* | 7/2007 | Prisco | B25J 9/1633 74/490.05 |
| 2008/0046122 | A1* | 2/2008 | Manzo | A61B 90/98 700/245 |
| 2008/0297092 | A1* | 12/2008 | Nihei | B25J 9/1638 318/568.22 |
| 2008/0309273 | A1* | 12/2008 | Kamiya | B25J 19/0004 318/563 |
| 2009/0088775 | A1* | 4/2009 | Swarup | A61B 34/71 700/264 |
| 2010/0168919 | A1* | 7/2010 | Okamoto | B25J 9/1643 700/275 |
| 2012/0245736 | A1* | 9/2012 | Bosscher | B25J 9/1607 700/262 |
| 2014/0276954 | A1 | 9/2014 | Hourtash | |
| 2014/0316431 | A1* | 10/2014 | Hourtash | A61B 34/37 606/130 |
| 2017/0095303 | A1 | 4/2017 | Hourtash et al. | |
| 2019/0060008 | A1* | 2/2019 | Bailey | A61B 17/29 |
| 2019/0327394 | A1* | 10/2019 | Ramirez Luna | H04N 23/51 |
| 2021/0121257 | A1* | 4/2021 | Yu | G16H 40/67 |
| 2021/0122041 | A1* | 4/2021 | Mottram | A61B 34/30 |
| 2024/0245477 | A1* | 7/2024 | Yu | A61B 34/25 |

FOREIGN PATENT DOCUMENTS

| | | |
|---|---|---|
| WO | 2006/124388 A1 | 11/2006 |
| WO | 2014/145471 A1 | 9/2014 |
| WO | 2019/117896 A1 | 6/2019 |
| WO | 2019/138111 A1 | 7/2019 |

OTHER PUBLICATIONS

Chiu, S. L., et al., "Task Compatibility of Manipulator Postures", The International Journal of Robotics Research, vol. 7, No. 5, Oct. 1988, pp. 13-21.
Dubey, R., et al., "Redundant robot control using task based performance measures", Journal of Robotic Systems, vol. 5, No. 5, Oct. 1, 1988, pp. 409-432.
European Search Report and Search Opinion received for EP Application No. 19949717.3, mailed on Sep. 26, 2023, 8 pages.
International Preliminary Report on Patentability for International Application No. PCT/US2019/062059 mailed May 5, 2022, 5 pages.
International Search Report and Written Opinion for International Application No. PCT/US2019/062059 mailed Jul. 14, 2020, 18 pages.
Jaime Martinez, "Manipulability Ellipsoids in Robotics," Published May 4, 2013 on Website: Engineer Jau; available online at: https://engineerjau.wordpress.com/2013/05/04/advanced-robotics-manipulability-ellipsoids/.
Non-Final Office Action received for U.S. Appl. No. 17/575,383, mailed on Apr. 26, 2023, 14 pages.
Notice of Allowance received for U.S. Appl. No. 16/663,277, mailed on Sep. 15, 2021, 9 pages.
Notice of Allowance received for U.S. Appl. No. 17/575,383, mailed on Oct. 31, 2023, 9 pages.
Office Action received for Japanese Patent Application No. 2022-523939, mailed on Sep. 22, 2023, 5 pages (English translation only).
Singh, J. R., et al., "Optimal synthesis of robot manipulators based on global kinematic parameters", Mechanism and Machine Theory, vol. 30, No. 4, May 1995, pp. 569-580.
Tsuneo Yoshikawa, "Manipulability of Robotic Mechanisms," The International Journal of Robotics Research, vol. 4, ssue 2, Jun. 1, 1985, pp. 3-9.
Notice of Preliminary Rejection received for Korean Patent Application No. 10-2022-7016788, mailed on Feb. 24, 2025, 12 pages (6 pages of Original Document and 6 pages of English Translation).

* cited by examiner

REGULATING JOINT SPACE VELOCITY OF A SURGICAL ROBOTIC ARM

CROSS-REFERENCE TO RELATED APPLICATIONS

This application is a continuation co-pending U.S. patent application Ser. No. 17/575,383, filed on Jan. 13, 2022, entitled "REGULATING JOINT SPACE VELOCITY OF A SURGICAL ROBOTIC ARM," which is a continuation of U.S. patent application Ser. No. 16/663,277, filed Oct. 24, 2019, entitled "REGULATING JOINT SPACE VELOCITY OF A SURGICAL ROBOTIC ARM," now U.S. Pat. No. 11,229,494, issued Jan. 25, 2022, which are hereby incorporated by reference in their entirety.

TECHNICAL FIELD

This disclosure relates to digital control techniques for giving an operator of a surgical robotic arm and end effector a feeling of uniform easiness when repositioning the end effector.

BACKGROUND

Minimally-invasive surgery (MIS), such as laparoscopic surgery, involves techniques intended to reduce tissue damage during a surgical procedure. For example, laparoscopic procedures typically involve creating a number of small incisions in the patient (e.g., in the abdomen), and introducing one or more tools and at least one endoscopic camera through the incisions into the patient. The surgical procedures are then performed by using the introduced tools, with the visualization aid provided by the camera. Generally, MIS provides multiple benefits, such as reduced patient scarring, less patient pain, shorter patient recovery periods, and lower medical treatment costs associated with patient recovery.

MIS may be performed with a surgical robotic system that includes several robotic arms. Each arm has a surgical tool or instrument at the end of which is an end effector, such as grasping jaws, scissors, and an endoscope camera, that are inserted into the patient's body at the surgical site. The surgical operations are performed upon the bodily tissue of the patient using the arms and end effectors which are manipulated "remotely" by an operator (e.g., a surgeon). The surgical robotic system ensures that position and orientation of the end effector will mimic the manipulation of a user input device (UID) in the hand of the surgeon. This is enabled by a digital control system that tracks the motion of the UID and in response calculates the appropriate commands to the motorized joints of the arm resulting in the movement of the end effector mimicking that of the hand-held UID.

SUMMARY

When an operator manipulates the end effector at the end of a surgical robotic arm (remotely via a UID in their hand), they may not have knowledge of which direction the end effector can be moved with greater easiness. They might expect that control of the end effector should be isotropic, that is able to move at the same speed in all directions and for all possible configurations (e.g., joint angles) of the arm. In fact, however, the surgical robotic arm is not isotropic. For any given configuration of the arm (including a given set of joint angles at which the arm currently finds itself in), the easiness of moving the end effector is not the same in all directions. Consider a person's actual arm—the person can swing their hand left to right faster than they can thrust it forward and backward. Even if a person has such an understanding of their body, they would not typically have the same understanding for the behavior of a surgical robotic arm.

Various aspects of the disclosure here are digital control methodologies that aim to produce a feeling of isotropicness or uniform easiness for the operator who is manipulating the end effector on a surgical robotic arm. This may enable the system to feel more natural to the operator.

In one aspect, a method for regulating joint space velocity of the surgical robotic arm has the following operations, performed by a programmed processor. For a given configuration of the surgical robotic arm, a task space velocity is received (e.g., linear or translational velocity, based on a UID tracking sequence). For each of the active joints of the arm, a potential joint velocity is computed by i) producing a vector having a norm of the received task space velocity and having an orientation that is along a longest principle axis of a velocity ellipsoid of the end effector and ii) applying inverse kinematic equations for the arm to the vector to produce the potential joint velocity. When the computed potential joint velocity exceeds a joint velocity limit of a respective joint, a ratio between i) the joint velocity limit and ii) the potential joint velocity is computed. The joint space velocity limit may be defined by the mechanical characteristics of the active (motorized) and passive joints, and may be greater than or less than the potential maximum joint space velocity that was computed. The ratio is then applied to (e.g., multiplied by) an initial joint space velocity, which may be a transformation of the received task space velocity into joint space, to produce a regulated joint space velocity (for the given surgical robotic arm configuration).

The regulated joint space velocity may provide a more uniform feeling of easiness to the operator who is manipulating the UID. This manner of controlling the end effector movement may give the operator a feeling of uniform easiness in all directions.

The above summary does not include an exhaustive list of all aspects of the present disclosure. It is contemplated that the disclosure includes all systems and methods that can be practiced from all suitable combinations of the various aspects summarized above, as well as those disclosed in the Detailed Description below and particularly pointed out in the Claims section. Such combinations may have particular advantages not specifically recited in the above summary.

BRIEF DESCRIPTION OF THE DRAWINGS

Several aspects of the disclosure here are illustrated by way of example and not by way of limitation in the figures of the accompanying drawings in which like references indicate similar elements. It should be noted that references to "an" or "one" aspect in this disclosure are not necessarily to the same aspect, and they mean at least one. Also, in the interest of conciseness and reducing the total number of figures, a given figure may be used to illustrate the features of more than one aspect of the disclosure, and not all elements in the figure may be required for a given aspect.

BRIEF DESCRIPTION OF THE DRAWINGS

Several aspects of the disclosure with reference to the appended drawings are now explained. Whenever the shapes, relative positions and other aspects of the parts described are not explicitly defined, the scope of the invention is not limited only to the parts shown, which are meant merely for the purpose of illustration. Also, while numerous details are set forth, it is understood that some aspects of the disclosure may be practiced without these details. In other instances, well-known circuits, structures, and techniques have not been shown in detail so as not to obscure the understanding of this description.

Figure 1:
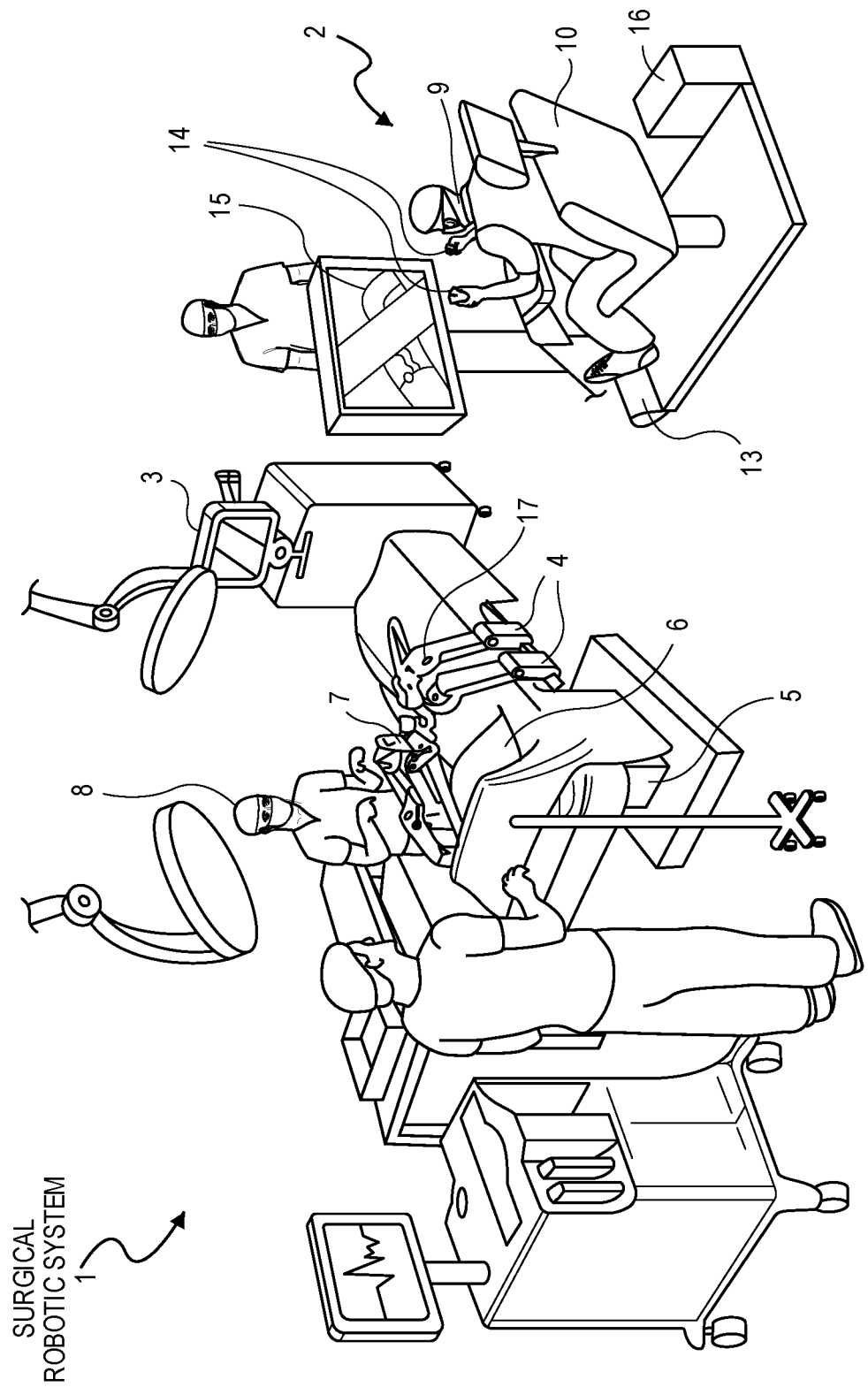
FIG. 1 is an overview schematic of an operating room arrangement with a surgical robotic system.

Referring to FIG. 1, this is a pictorial view of an example surgical robotic system 1 in an operating arena. The robotic system 1 includes a user console 2, a control tower 3, and one or more surgical robotic arms 4 that may be mounted to a surgical robotic platform 5, e.g., a table, a bed, etc. FIG. 1 shows an example where the arms 4 are mounted to the table or bed on which the patient rests. The system 1 can incorporate any number of devices, tools, or accessories used to perform surgery on a patient 6. For example, the system 1 may include one or more surgical tools 7 used to perform surgery. A surgical tool 7 may be an end effector that is attached to a distal end of a surgical arm 4, for executing a surgical procedure.

Each surgical tool 7 may be manipulated manually, robotically, or both, during the surgery. For example, the surgical tool 7 may be a tool used to enter, view, or manipulate an internal anatomy of the patient 6. In an embodiment, the surgical tool 7 is a grasper that can grasp tissue of the patient. The surgical tool 7 may be controlled manually, by a bedside operator 8; or it may be controlled robotically, via actuated movement of the surgical robotic arm 4 to which it is attached. The robotic arms 4 are shown as a table-mounted system, but in other instances the arms 4 may be mounted in a cart, ceiling or sidewall, or in another suitable structural support.

Generally, a remote operator 9, such as a surgeon or other operator, may use the user console 2 to remotely manipulate the arms 4 and/or the attached surgical tools 7, e.g., teleoperation. The user console 2 may be located in the same operating room as the rest of the system 1, as shown in FIG. 1. In other environments however, the user console 2 may be located in an adjacent or nearby room, or it may be at a remote location, e.g., in a different building, city, or country. The user console 2 may comprise a seat 10, foot-operated controls 13, one or more handheld user input devices, UID 14, and at least one user display 15 that is configured to display, for example, a view of the surgical site inside the patient 6. In the example user console 2, the remote operator 9 is sitting in the seat 10 and viewing the user display 15 while manipulating a foot-operated control 13 and a handheld UID 14 in order to remotely control the arms 4 and the surgical tools 7 (that are mounted on the distal ends of the arms 4).

In some variations, the bedside operator 8 may also operate the system 1 in an "over the bed" mode, in which the beside operator 8 (user) is now at a side of the patient 6 and is simultaneously manipulating a robotically-driven tool (end effector as attached to the arm 4), e.g., with a handheld UID 14 held in one hand, and a manual laparoscopic tool. For example, the bedside operator's left hand may be manipulating the handheld UID to control a robotic component, while the bedside operator's right hand may be manipulating a manual laparoscopic tool. Thus, in these variations, the bedside operator 8 may perform both robotic-assisted minimally invasive surgery and manual laparoscopic surgery on the patient 6.

During an example procedure (surgery), the patient 6 is prepped and draped in a sterile fashion to achieve anesthesia. Initial access to the surgical site may be performed manually while the arms of the robotic system 1 are in a stowed condition or withdrawn condition (to facilitate access to the surgical site). Once access is completed, initial positioning or preparation of the robotic system 1 including its arms 4 may be performed. Next, the surgery proceeds with the remote operator 9 at the user console 2 utilizing the foot-operated controls 13 and the UIDs 14 to manipulate the various end effectors and perhaps an imaging system, to perform the surgery. Manual assistance may also be provided at the procedure bed or table, by sterile-gowned bedside personnel, e.g., the bedside operator 8 who may perform tasks such as retracting tissues, performing manual repositioning, and tool exchange upon one or more of the robotic arms 4. Non-sterile personnel may also be present to assist the remote operator 9 at the user console 2. When the procedure or surgery is completed, the system 1 and the user console 2 may be configured or set in a state to facilitate post-operative procedures such as cleaning or sterilization and healthcare record entry or printout via the user console 2.

In one embodiment, the remote operator 9 holds and moves the UID 14 to provide an input command to move a robot arm actuator 17 in the robotic system 1. The UID 14 may be communicatively coupled to the rest of the robotic system 1, e.g., via a console computer system 16. The UID 14 can generate spatial state signals corresponding to movement of the UID 14, e.g., position and orientation of the handheld housing of the UID, and the spatial state signals may be input signals to control a motion of the robot arm actuator 17. The robotic system 1 may use control signals derived from the spatial state signals, to control proportional motion of the actuator 17. In one embodiment, a console processor of the console computer system 16 receives the spatial state signals and generates the corresponding control signals. Based on these control signals, which control how the actuator 17 is energized to move a segment or link of the arm 4, the movement of a corresponding surgical tool that is attached to the arm may mimic the movement of the UID 14. Similarly, interaction between the remote operator 9 and the UID 14 can generate for example a grip control signal that causes a jaw of a grasper of the surgical tool 7 to close and grip the tissue of patient 6.

The surgical robotic system 1 may include several UIDs 14, where respective control signals are generated for each UID that control the actuators and the surgical tool (end effector) of a respective arm 4. For example, the remote operator 9 may move a first UID 14 to control the motion of an actuator 17 that is in a left robotic arm, where the actuator responds by moving linkages, gears, etc., in that arm 4. Similarly, movement of a second UID 14 by the remote operator 9 controls the motion of another actuator 17, which in turn moves other linkages, gears, etc., of the robotic system 1. The robotic system 1 may include a right arm 4 that is secured to the bed or table to the right side of the patient, and a left arm 4 that is at the left side of the patient. An actuator 17 may include one or more motors that are controlled so that they drive the rotation of a joint of the arm 4, to for example change, relative to the patient, an orientation of an endoscope or a grasper of the surgical tool 7 that is attached to that arm. Motion of several actuators 17 in the same arm 4 can be controlled by the spatial state signals generated from a particular UID 14. The UIDs 14 can also control motion of respective surgical tool graspers. For example, each UID 14 can generate a respective grip signal to control motion of an actuator, e.g., a linear actuator, which opens or closes jaws of the grasper at a distal end of surgical tool 7 to grip tissue within patient 6.

In some aspects, the communication between the platform 5 and the user console 2 may be through a control tower 3, which may translate user commands that are received from the user console 2 (and more particularly from the console computer system 16) into robotic control commands that transmitted to the arms 4 on the robotic platform 5. The control tower 3 may also transmit status and feedback from the platform 5 back to the user console 2. The communication connections between the robotic platform 5, the user console 2, and the control tower 3 may be via wired and/or wireless links, using any suitable ones of a variety of data communication protocols. Any wired connections may be optionally built into the floor and/or walls or ceiling of the operating room. The robotic system 1 may provide video output to one or more displays, including displays within the operating room as well as remote displays that are accessible via the Internet or other networks. The video output or feed may also be encrypted to ensure privacy and all or portions of the video output may be saved to a server or electronic healthcare record system.

Figure 3:
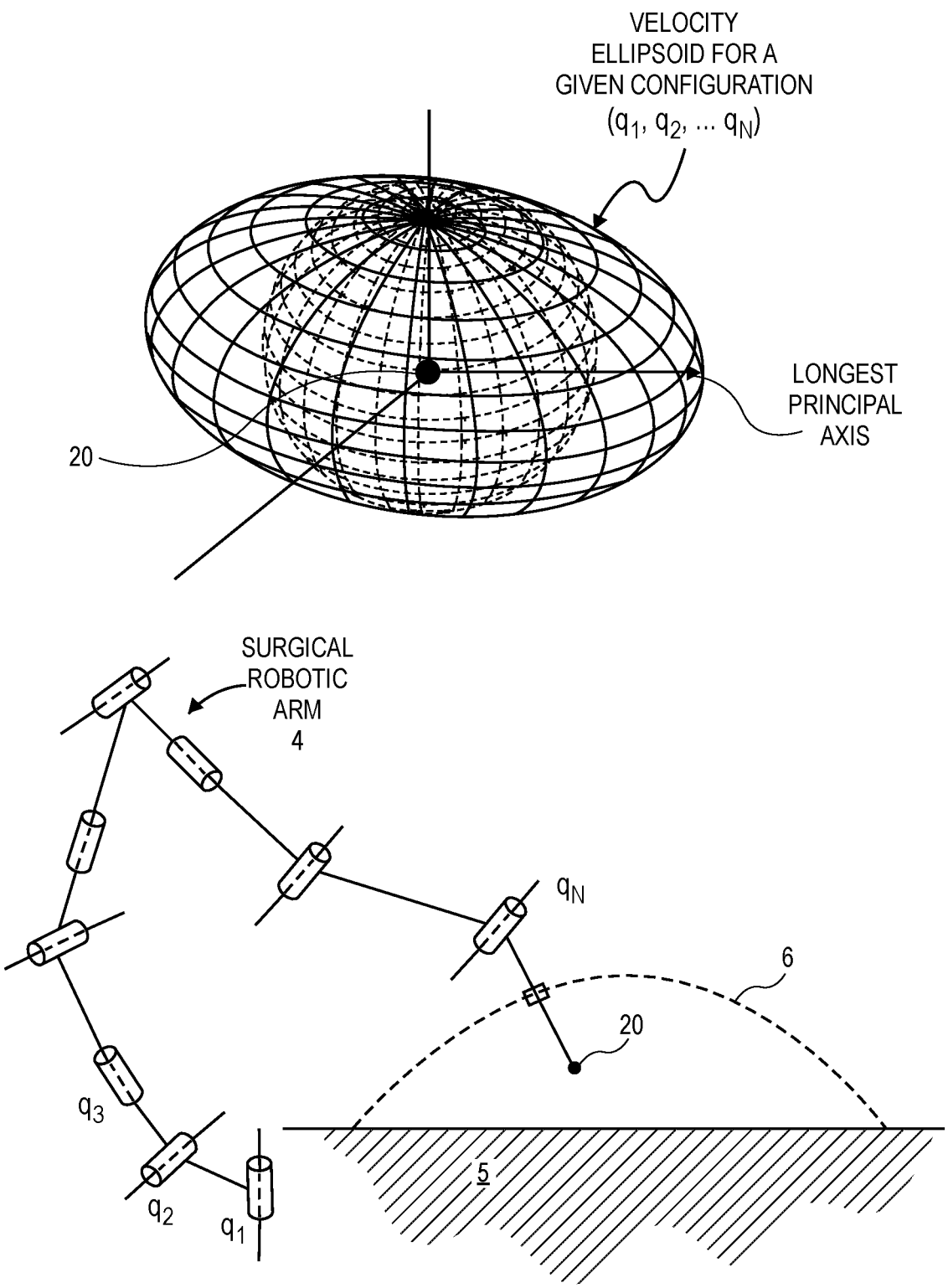
FIG. 3 depicts an example surgical robotic arm in action, and a velocity ellipsoid for a given configuration of the arm.

The surgical robotic arm 4 is a kinematically redundant manipulator in that it has a number of joints numbering at least seven that may be assigned joint position variables q1, q2, ... qN. The joints connect their adjacent, rigid links into a sequence, for example as depicted in FIG. 3, ending at a distal tip or end effector 20. The arm 4 is articulated so that the end effector 20 is located inside a body cavity of the patient 6. The end effector 20 is part of the surgical tool 7—see FIG. 1—that is attached at the joint qN. Some of the joints may be passive with mechanical constraints, while others are active or motorized. Some of the joints may be revolute while others may be prismatic. A joint position variable represents the relative displacement (e.g., angular, linear) between the adjacent links of a joint.

A coordinate system referred to as task space may be defined in which the end effector 20 or tip moves; this movement is governed by the joint position variables q1, q2, ... qN as a whole, which may form a joint vector in a coordinate system referred to as a "joint space." A set of forward kinematic equations define a function that determines a "task space" Cartesian position and orientation of the end effector 20 in terms of the joint space (positions of the joints of the arm 4). A set of inverse kinematic equations define the reverse function, determining the values of the joint position variables q1, q2, ... qN in terms of the task space position and orientation of the end effector 20.

Figure 2:
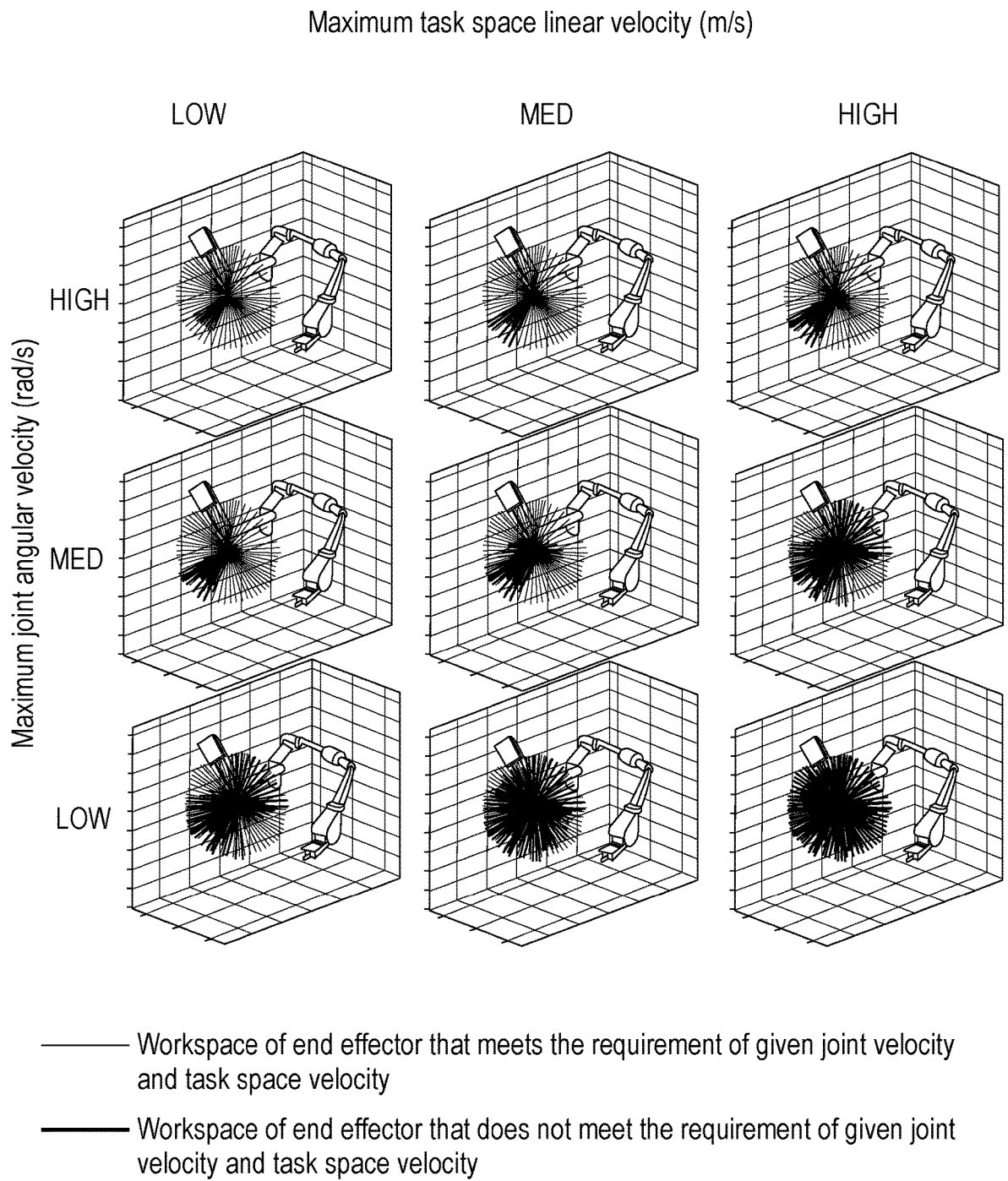
FIG. 2 illustrates how the regions or directions of end effector linear velocity are affected by the maximum end effector velocity that is required, and for different surgical robotic arm configurations having different maximum joint velocities.

More relevant to considerations of easiness of manipulating the end effector 20 is the velocity kinematics of the surgical robotic arm 4. This defines the relationship between linear velocity of the end effector 20 (task space linear velocity) and joint velocity variables dq1/dt, dq2/dt, ... dqN/dt (joint angular velocity, and also joint linear velocity if the arm contains prismatic joints). In this regard, FIG. 2 is used to depict several concepts. First, it illustrates how the maximum attainable velocity of the end effector 20 (when the arm 4 is being driven by the control system) is not uniform in all directions. This is due to the multi-link, multi-joint nature of the surgical robotic arm 4 and the fact that the end effector 4 is not constrained to move in any direction (though of course it is limited in velocity due to the motorized joints having finite power). The directions in which the end effector 20 can be driven at a given maximum task space velocity are limited—there are directions in which the end effector 20 cannot be driven at that velocity, as seen in the nine examples shown. FIG. 2 also illustrates three columns corresponding to three different maximum task space velocities. In each column, it can be seen how the workspace that can meet the given maximum task space velocity increases as a function of the available maximum joint velocity. If the available maximum joint velocity is increased, then there are more directions in which the desired maximum task space velocity can be met.

Considering the three rows in FIG. 2, each row illustrates how to expand the workspace in which a maximum task space velocity can be met, namely by lowering the maximum task space velocity. Thus, to produce a near isotropic system in which there is uniform easiness of moving the end effector 20 in most if not all directions, FIG. 2 suggests that the maximum task space velocity needs to be lowered sufficiently, while the maximum joint space velocity needs to be high enough. There is a need to link these two aspects, namely maximum joint velocity (which is dictated for the most part by motor power and transmission rations in the active joints) and maximum task space velocity (which may come from clinical needs), in order to solve the problem of how to ensure a feeling of isotropic easiness in moving the end effector 20 on the surgical robotic arm 4. It may also be desirable to regulate the task space velocity so that a given joint velocity requirement can be met, and the feeling of isotropic easiness is achieved. A systematic approach to solve such problems is now presented in connection with FIG. 3 and the flow diagram of FIG. 4, in which the joint space velocity is limited or regulated under certain situations, thereby enabling the operator to feel isotropic movement (when manipulating the end effector 20 remotely via the handheld UID 14.

FIG. 3 shows an example surgical robotic arm 4 having joints associated with respective joint position variables q1, q2, ... qN, and the end effector 20 which is positioned inside a body cavity of the patient 6 (who is lying on a table, as part of the surgical robotic platform 5). For any given configuration of the arm 4, where "configuration" here refers to a particular instance of the set of joint variables q1, q2, ... qN, a velocity ellipsoid can be computed which is a 3D surface that defines the available maximum task space linear velocity at which the end effector 20 can be driven, in the various directions defined by the 3D surface. This may also be referred to as a manipulability ellipsoid. The ellipsoid may be computed using the inverse Jacobian of the arm 4. The longest principal axis of the velocity ellipsoid is indicated in the figure, and it represents the direction in which the maximum task space linear velocity can be achieved. If there is a configuration for which the computed ellipsoid happens to be essentially a sphere (shown in dotted lines), then in that configuration the arm 4 is deemed isotropic—the operator will experience uniform easiness in all directions.

In one aspect, the digital control algorithm that is continually updating motor control commands that control the active or motorized joints of the surgical robotic arm is modified, by performing the following method for regulating joint space velocity of the arm. A goal of the process is for the operator to experience uniform easiness in all directions, as the operator manipulates the end effector 20 via the handheld UID 14. Referring to the process flow diagram of FIG. 4, which refers to operations performed by a programmed processor in a surgical robotic system, a longest principal axis of a velocity ellipsoid for a given surgical robotic arm configuration is determined (operation 404). This is also referred to as a manipulability ellipsoid, ME, or a linear velocity ME. The longest principal axis may however be computed directly without having to compute the entire ME, or it may be determined based on having first computed the ME using an inverse Jacobian for the arm 4 and then examined the ME to determine the longest principal axis.

Next, a task space velocity (e.g., received based on a current element of a UID tracking sequence) is applied to the longest principal axis, to produce a new vector. This new vector may be considered to be a maximum or worst case task space velocity that is in the direction of the longest principal axis (or longest principal semi-axis if the origin of the ellipsoid is at (0,0,0). If the ME is normalized to 1, then a conversion of this vector may be needed to find the maximum task space linear velocity (e.g., in units of meters/second) that is on the longest principal axis. The maximum task space velocity is then applied to compute (or is transformed into) a potential joint space velocity (operation 406). This may be done using inverse kinematics equations (including an inverse Jacobian) for the arm 4. The potential joint space velocity represents how fast the active joints need to change their positions in order for the end effector 20 to exhibit the maximum task space velocity.

The process then continues with operation 408 in which a ratio of i) the potential joint space velocity and ii) a joint space velocity limit for the surgical robotic arm 4, is computed. The joint space velocity limit may be a vector whose components or values refer to maximum velocities of the active joints, respectively, of the surgical robotic arm 4. In one aspect, the joint space velocity limit (vector) may be unchanged for the various configurations of the arm 4. The ratio is then applied to (e.g., multiplied by) an initial joint space velocity, which may be a transformation of the received task space velocity into joint space velocity, to produce a regulated joint space velocity (operation 410).

If the joint space velocity limit of the surgical robotic arm configuration is greater than the potential joint space velocity, then the regulated joint space velocity is made to be the same as the initial joint space velocity (that resulted from a transformation of the received task space velocity into joint space). In other words, the initial joint space velocity in that case may be applied unchanged, to update the motor control commands. But if the joint space velocity limit is less than the potential joint space velocity, then a ratio that is less than one is applied, as a down scaling factor to the initial joint space velocity. As a result, a feeling of uniform easiness in all directions is achieved, since the digital control algorithm will in this manner automatically limit any requested joint space velocity to not exceed the joint space velocity limit. An example of how this would work is as follows. Let's consider that the digital control algorithm detects a changed configuration of the arm 4, and receives a new task space velocity that is in accordance with a UID tracking sequence (so that the end effector 20 can mimic the tracked position and orientation of the UID 14). The control algorithm transforms the new task space velocity to a new or initial joint space velocity (e.g., using inverse kinematics including the inverse Jacobian). In a conventional approach, the algorithm would simply apply the new joint space velocity as-is, to update a number of motor control commands that control the motorized joints of the arm 4. Here however, for each of the plurality of active joints in the arm 4, a respective potential joint velocity is computed, by applying the received, new task space velocity along a longest principal axis of the velocity ellipsoid of the current configuration of the arm 4 (e.g., producing a new vector having a norm of the new task space velocity and oriented in the direction of the longest principal axis. When the respective potential joint velocity exceeds a joint velocity limit of a respective joint, a ratio between i) the joint velocity limit and ii) the respective potential joint velocity is computed.

A respective regulated joint velocity for each of the plurality of active joints is then generated, based on the ratio. In such a situation therefore, the joint space velocity limit is less than the potential joint space velocity, and as a result of applying the ratio, the regulated joint space velocity is less than the joint space velocity limit. In other words, if the potential joint space velocity exceeds the joint space velocity limit by some threshold amount (as determined by for example comparing the potential joint space velocity to the joint space velocity limit), then the algorithm modifies the new joint space velocity by applying the ratio to it, so as to not exceed the joint space velocity limit (before applying the modified new joint space velocity to update the motor control commands). The modified new or regulated joint space velocity is applied to update a plurality of motor control commands that control a plurality of motorized joints (the active joints) of the surgical robotic arm 4. The updated motor control commands serve to control the motorized joints of the arm 4 so that the end effector 20 is driven to a new task space position in accordance with a new UID position (indicated by the UID tracking sequence).

The process above may repeat for a new task space velocity, by computing an updated ratio of i) the updated potential joint space velocity and ii) the joint space velocity limit for the surgical robotic arm and applying the updated ratio to a transformation of the new task space velocity to produce another regulated joint space velocity. This may be done without having to re-compute the longest principal axis, if the configuration of the arm 4 does not change.

When there are two or more joints, in the plurality of active joints, for which the respective potential joint velocity exceeds a joint velocity limit of the respective joint, several ratios are computed, one for each of the two or more joints, respectively (using the approach described above). Next, the smallest of these ratios is selected, or in other words, the active joint whose respective potential joint velocity exceeds its joint velocity limit the most. For example, if joints a and b both exceed their respective limits, but joint a exceeds its limit more than joint b exceeds its limit, then joint a is selected to compute the ratio. In other words, the ratio of the respective potential joint velocity of joint a to the joint velocity limit (of joint a) is then selected, to be used in generating the respective regulated joint velocities for all of the active joints. As mentioned above, this may be done by multiplying the initial joint space velocities of all of the active joints, by the selected ratio (of joint a).

Figure 4:
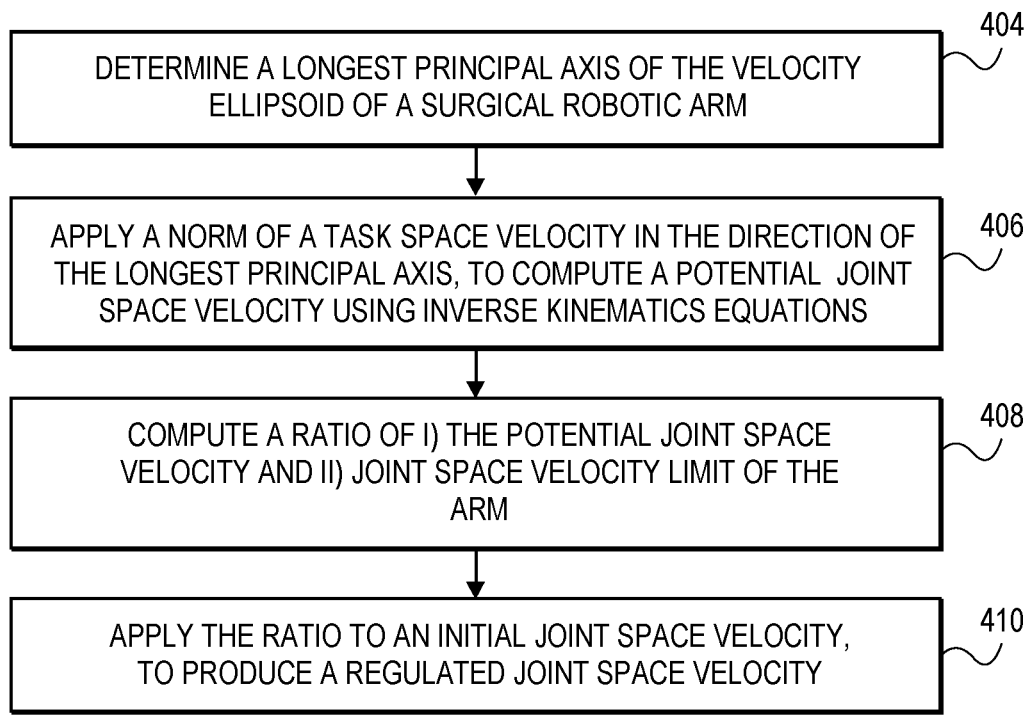
FIG. 4 is a flow diagram of a process for regulating joint space velocity of a surgical robotic arm.

The process in FIG. 4 may continue as follows, in situations where the configuration of the arm 4 does not change. Upon receiving another task space velocity of the end effector (that is on a distal end of the surgical robotic arm 4), another respective potential joint velocity is computed for each of the active joints as in block 406, by applying said another task space velocity along the longest principle axis of the velocity ellipsoid (because the configuration of the arm has not changed, the longest principle axis need not be re-calculated, i.e., block 404 may be omitted.

If another respective potential joint velocity does not exceed the joint velocity limit of the respective joint, then another respective potential joint velocity is left unchanged (block 410 is omitted essentially, or equivalently the ratio in block 410 is set to unity), else if said another respective potential joint velocity does exceed the joint velocity limit of the respective joint, then a new ratio is computed in block 408.

Note that in some situations, a new ratio can be computed without having to compute a new potential joint space velocity that corresponds to a new task space velocity. That is in contrast to when the configuration of the surgical robotic arm changes—the new ratio in that case needs to be computed using an updated, longest principal axis (being that of an ellipsoid at the new configuration). The new ratio may be computed as follows, in situations where for instance only the norm of the task space velocity changes (its orientation remains unchanged relative to an immediately prior or previous task space velocity). After receiving a new task space velocity v_b, compare it to the previous task space velocity v_a, and then compute the new ratio by scaling the previous ratio with v_a/v_b. For example, if the previous ratio is 0.6, and v_b=2*v_a, then the new ratio would be 0.3. A reason behind this is because the joint space velocity limit is fixed, and the longest principal axis has not changed, and the only change (relative to the previous task space velocity) is in the norm of the new task space velocity.

The foregoing description, for purposes of explanation, uses specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, and they thereby enable others skilled in the art to best utilize the invention in its various embodiments with various modifications that are suited to the particular use contemplated.

What is claimed is:

1. A method for regulating joint space velocity of a surgical robotic arm, the method comprising:
   computing a potential joint space velocity of a surgical robotic arm based on a task space velocity;
   computing a ratio of i) the potential joint space velocity and ii) a joint space velocity limit for the surgical robotic arm; and
   driving the surgical robotic arm based on the ratio.

2. The method of claim 1 wherein the joint space velocity limit is less than the potential joint space velocity, the method further comprising
   applying the ratio to an initial joint space velocity to produce a regulated joint space velocity,
   and wherein driving the surgical robotic arm based on the ratio comprises driving the surgical robotic arm based on the regulated joint space velocity.

3. The method of claim 1 wherein driving the surgical robotic arm comprises
   applying the ratio to update a plurality of motor control commands that control a plurality of motorized joints of the surgical robotic arm.

4. The method of claim 1 further comprising:
   transforming a new task space velocity to a new potential joint space velocity;
   computing a new ratio based on i) said ratio and ii) a comparison between the new task space velocity and a previous task space velocity; and
   driving the surgical robotic arm based on the new ratio.

5. The method of claim 4 wherein driving the surgical robotic arm comprises
   applying the new ratio to update a plurality of motor control commands that control a plurality of motorized joints of the surgical robotic arm.

6. The method of claim 1 further comprising:
   in response to detecting a changed configuration of the surgical robotic arm, computing a longest principal axis of a velocity ellipsoid for the changed configuration;
   receiving a new task space velocity and producing a new vector, the new vector having a norm of the new task space velocity and an orientation of the longest principal axis, and based on the new vector computing an updated potential joint space velocity;
   computing an updated ratio of i) the updated potential joint space velocity and ii) the joint space velocity limit; and
   applying the updated ratio to a transformation of the new task space velocity into joint space, which produces an updated regulated joint space velocity.

7. The method of claim 6 further comprising
   updating a plurality of motor control commands that control a plurality of motorized joints of the surgical robotic arm using the updated regulated joint space velocity, which causes an end effector on the surgical robotic arm to be driven to a new task space position in accordance with a new user input device position.

8. The method of claim 1 wherein computing the potential joint space velocity comprises applying a norm of the task space velocity along a longest principal axis of a velocity ellipsoid for the surgical robotic arm, the method further comprising computing the velocity ellipsoid using an inverse Jacobian for the surgical robotic arm.

9. A surgical robotic system comprising:
   a surgical robotic arm; and
   a programmed processor that is to
      a) produce a vector based on a task space velocity in a first configuration of a surgical robotic arm, and compute a potential joint space velocity based on the vector,
      b) compute a ratio of i) the potential joint space velocity and ii) a joint space velocity limit of the surgical robotic arm, and
      c) drive the surgical robotic arm using the ratio.

10. The surgical robotic system of claim 9 wherein the programmed processor is to:
    determine a second configuration of the surgical robotic arm, in response to an end effector on the surgical robotic arm being guided to a new task space position; and
    repeat operations a)-c) for the second configuration.

11. The surgical robotic system of claim 9 wherein the first configuration comprises
    data on current joint space position of each of a plurality of joints of the surgical robotic arm.

12. The surgical robotic system of claim 11 wherein the first configuration further comprises
    data on joint space velocity limit of each of a plurality of motorized joints of the surgical robotic arm.

13. The surgical robotic system of claim 9 wherein the joint space velocity limit is less than the potential joint space velocity, and the programmed processor is further configured to apply the ratio to an initial joint space velocity to produce a regulated joint space velocity that is less than the potential joint space velocity.

14. The surgical robotic system of claim 13 wherein the processor is further configured to:
   compute a new task space velocity in accordance with a user input device tracking sequence;
   transform the new task space velocity to a new potential joint space velocity without recomputing a longest principal axis of a velocity ellipsoid;
   compute a new ratio as in b) using the new potential joint space velocity; and
   use the new ratio to drive the surgical robotic arm.

15. The surgical robotic system of claim 9 wherein the programmed processor drives the surgical robotic arm by updating, using the ratio, a plurality of motor control commands that control a plurality of motorized joints of the surgical robotic arm.

16. The surgical robotic system of claim 9 wherein the programmed processor is configured to compute the ratio by:
   for each motorized joint of a plurality of motorized joints in the surgical robotic arm, computing a potential joint velocity along a longest principal axis of a velocity ellipsoid based on the task space velocity; and
   when the potential joint velocity exceeds a joint velocity limit of the motorized joint, computing the ratio as between i) the joint velocity limit of the motorized joint and ii) the potential joint velocity.

17. A method for regulating velocity of a surgical robotic arm, the method comprising:
   a) for each active joint of a plurality of active joints of a surgical robotic arm, computing a respective potential joint velocity based on a task space velocity;
   b) if the respective potential joint velocity exceeds a joint velocity limit of each active joint, then computing a ratio for each active joint as between i) the joint velocity limit and ii) the respective potential joint velocity, else setting the ratio of each active joint to unity; and
   c) driving the surgical robotic arm in accordance with the ratio for each active joint, of the plurality of active joints.

18. The method of claim 17 wherein the respective potential joint velocity comprises a linear velocity or an angular velocity.

19. The method of claim 17 wherein when there are two or more active joints, in the plurality of active joints, for which the respective potential joint velocity exceeds the joint velocity limit of each active joint, and two or more ratios are computed for the two or more active joints, respectively, the method further comprises selecting the smallest of the two or more ratios for use in driving the surgical robotic arm in c).

20. The method of claim 17 further comprising:
   receiving a further task space velocity;
   for each active joint of the plurality of active joints, computing a further respective potential joint velocity based on the further task space velocity; and
   if the further respective potential joint velocity does not exceed the joint velocity limit of each active joint, then leaving the further respective potential joint velocity unchanged to use in driving the surgical robotic arm,
   else if the further respective potential joint velocity does exceed the joint velocity limit, then computing a new ratio between i) the joint velocity limit and ii) the further respective potential joint velocity, and using the new ratio in driving the surgical robotic arm.

* * * * *